United States Patent
Fallin et al.

(10) Patent No.: US 8,961,604 B2
(45) Date of Patent: Feb. 24, 2015

(54) FIXATION IMPLANT AND METHOD

(71) Applicant: Smith & Nephew, Inc., Memphis, TN (US)

(72) Inventors: T. Wade Fallin, Hyde Park, UT (US); M Mary Sinnott, North Logan, UT (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 13/630,703

(22) Filed: Sep. 28, 2012

(65) Prior Publication Data

US 2014/0094911 A1    Apr. 3, 2014

(51) Int. Cl.
*A61F 2/08* (2006.01)
*A61B 17/04* (2006.01)

(52) U.S. Cl.
USPC ............... 623/13.14; 623/13.11; 623/13.17; 606/86 R; 606/300

(58) Field of Classification Search
USPC ............ 623/13.11–13.2, 21.11–21.19, 23.48; 606/86 R, 300–321
See application file for complete search history.

(56) References Cited

U.S. PATENT DOCUMENTS

| | | | |
|---|---|---|---|
| 4,605,414 A | 8/1986 | Czajka | |
| 4,668,233 A | 5/1987 | Seedhom et al. | |
| 4,927,421 A | 5/1990 | Goble et al. | |
| 5,062,843 A | 11/1991 | Mahony, III | |
| 5,211,647 A | 5/1993 | Schmieding | |
| 5,470,334 A | 11/1995 | Ross et al. | |
| 5,609,595 A | 3/1997 | Penning | |
| 5,709,687 A | 1/1998 | Penning | |
| 6,461,373 B2 | 10/2002 | Wyman et al. | |
| 6,544,281 B2 | 4/2003 | Elattrache et al. | |
| 6,629,977 B1 | 10/2003 | Wolf | |
| 6,875,216 B2 | 4/2005 | Wolf | |
| 7,063,717 B2 | 6/2006 | St. Pierre et al. | |
| 7,147,651 B2 | 12/2006 | Morrison et al. | |
| 7,322,986 B2 | 1/2008 | Wolf | |
| 8,021,367 B2 | 9/2011 | Bourke et al. | |
| 2008/0046009 A1 | 2/2008 | Albertorio et al. | |
| 2008/0188935 A1 | 8/2008 | Saylor et al. | |
| 2010/0076504 A1* | 3/2010 | McNamara et al. | 606/86 R |

OTHER PUBLICATIONS

Blitz, et al. "*Plantar Plate Repair of the Second Metatarsophalangeal Joint: Technique and Tips*" Journal of Foot & Ankle Surgery, 2004 43(4):266-270.

Coughlin, et al. "*Second MTP Joint Instability: Grading of the Deformity and Description of Surgical Repair of Capsular Insufficiency*" The Physician and Sportmedicine, Sep. 3, 2011, 39(3):132-141.

(Continued)

*Primary Examiner* — Yashita Sharma
(74) *Attorney, Agent, or Firm* — David A. Chambers

(57) ABSTRACT

A fixation implant and associated methods are presented. The fixation implant includes a shaft extending from a first end portion to a second end portion and having an intermediate portion therebetween. The intermediate portion is generally smooth and the end portions are threaded. The method includes use of the fixation implant for repair of a metapodial phalangeal joint of a human extremity. The method includes: forming a bone tunnel in a bone; approximating material near the bone tunnel; and threading the fixation implant into the bone tunnel in interference fashion to secure the material relative to the bone tunnel. The fixation implant may be cut such that the end portion is flush with the bone.

17 Claims, 13 Drawing Sheets

(56) References Cited

OTHER PUBLICATIONS

Fleming and Camasta, "*Plantar Plate Dysfunction*" Chapter 4, (2002) pp. 22-28, http://www.podiatryinstitute.com/pdfs/Update_2002/2002_04.pdf.

Gregg et al., "Plantar Plate Repair and Weil Osteotomy for Metatarsophalangeal Joint Instability" Foot and Ankle Surgery, (2007) 13:116-121.

Nery et al., "*Lesser Metatarsophalangeal Joint Instability: Prospective Evaluation and Repair of Plantar Plate and Capsular Insufficiency*" Foot and Ankle International, Apr. 2012 vol. 33(4):301-311.

Weil, et al. "Anatomic Plantar Plate Repair ing the Weil Metatarsal Osteotomy Approach" Foot and Ankle Specialist, Jun. 22, 2011, 4:145-150. Originally published online on Mar. 18, 2011 http://fas.sagepub.com/content/4/3/145.

\* cited by examiner

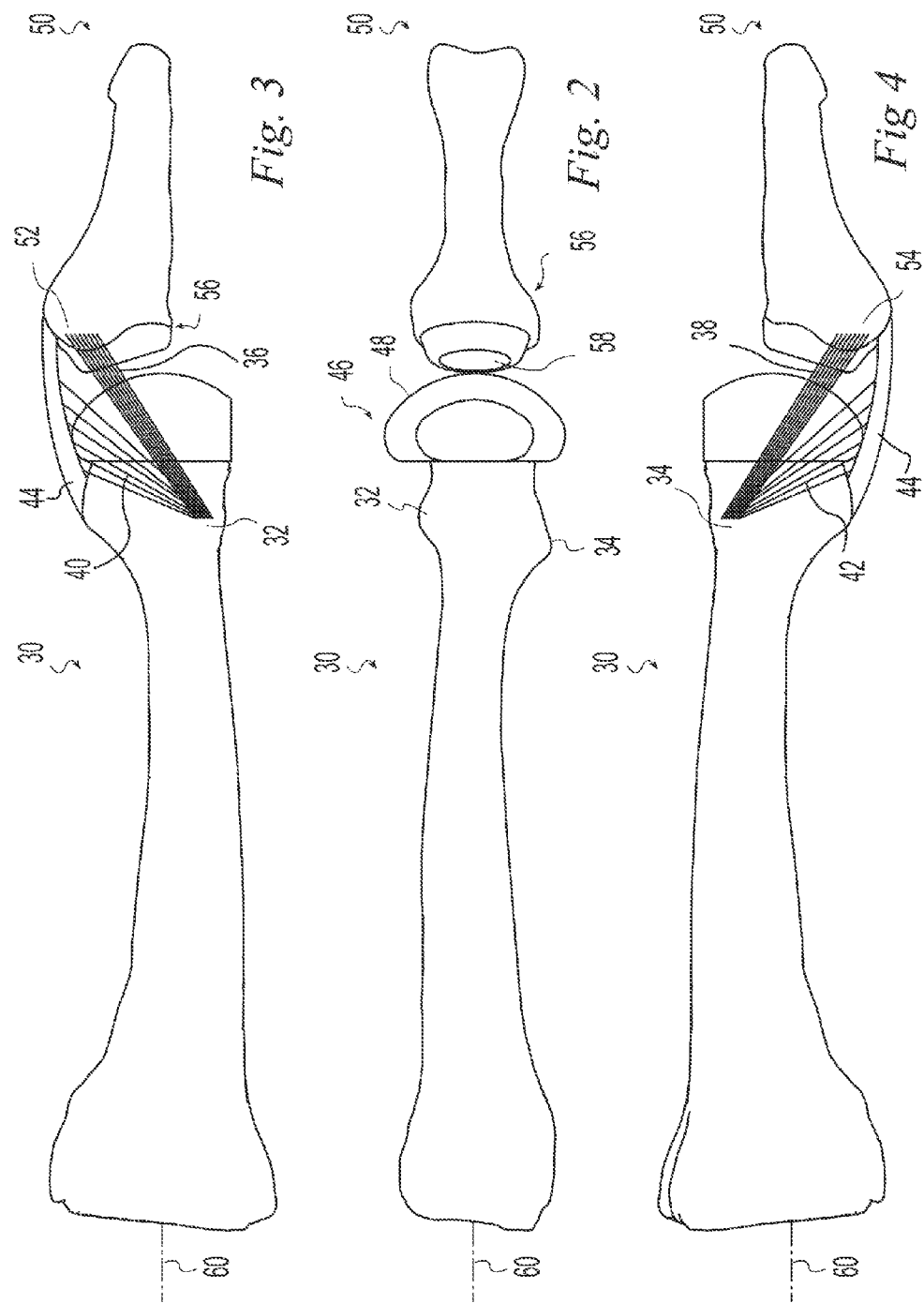

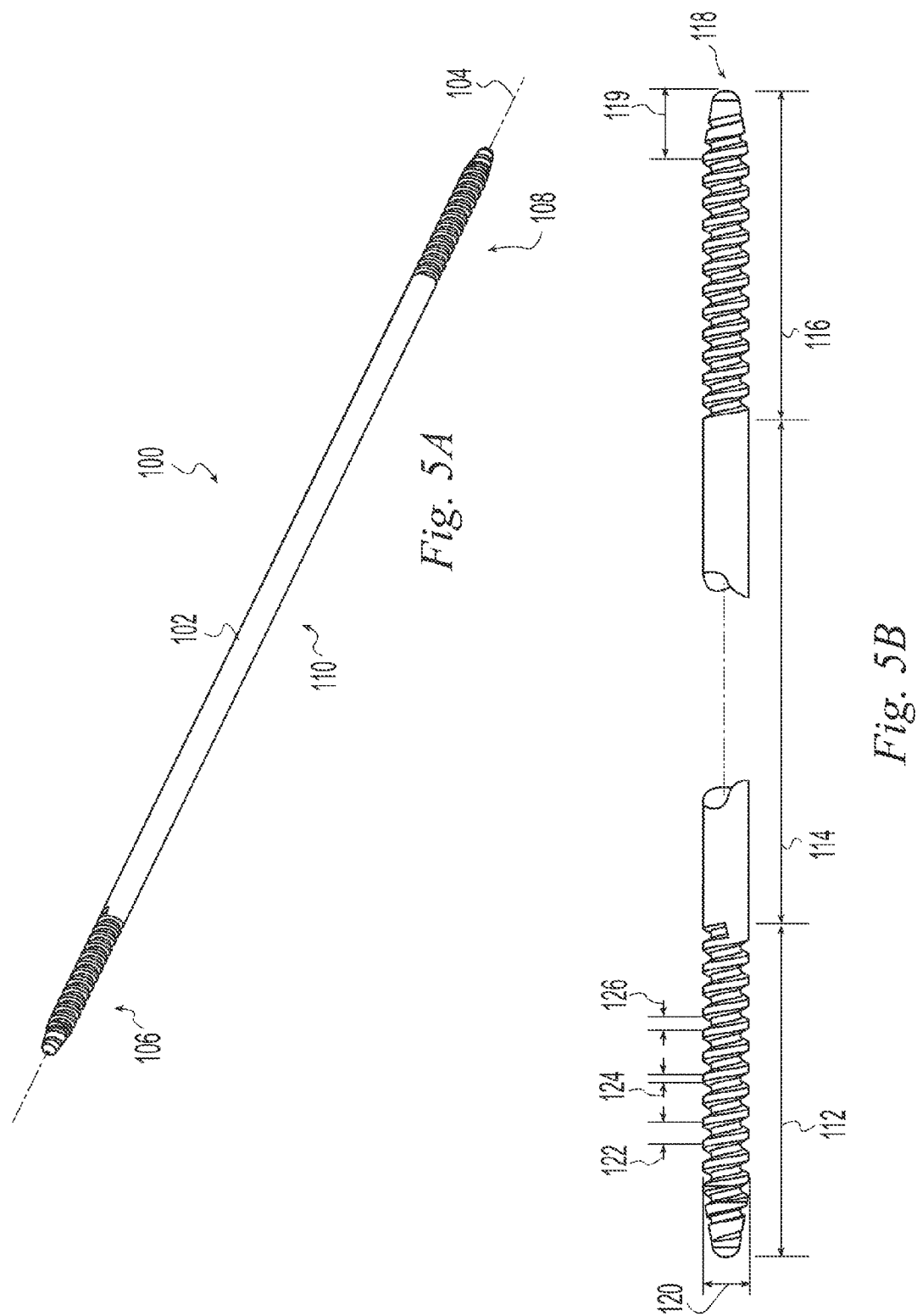

US 8,961,604 B2

FIXATION IMPLANT AND METHOD

FIELD OF THE INVENTION

The invention relates to fixation implants and methods for making and using them.

BACKGROUND

Various conditions may affect skeletal joints such as the elongation, shortening, detachment or rupture of soft tissues associated with the joint. Joint function may be restored by reconstruction of the soft tissues associated with the joint for example by reattaching soft tissue and/or fixing grafts at the joint.

SUMMARY

The present invention provides fixation implants and methods for making and using them.

In one aspect of the invention, a fixation implant includes an elongated shaft extending from a first end portion to a second end portion and having an intermediate portion between the first and second end portions. The intermediate portion is substantially smooth and the end portions are threaded. The shaft is made of a polymer and the first and second end portions are separable from the intermediate portion by cutting.

In another aspect of the invention, a method of reconstructing soft tissue of a metapodial phalangeal joint of a human extremity having a metapodial bone and a proximal phalanx includes forming a metapodial bone tunnel in the metapodial bone, forming a phalangeal bone tunnel in the proximal phalanx, placing a graft between the metapodial and phalangeal bone tunnels, threading a first end of a double ended fixation implant into one of the metapodial bone tunnel and phalangeal bone tunnel in interference fashion to secure the graft relative to the bone tunnel, separating the first end from a shaft of the fixation implant, threading a second end of the fixation implant into the other of the metapodial bone tunnel and phalangeal bone tunnel in interference fashion to secure the graft relative to the bone tunnel, and separating the second end from the shaft of the fixation implant.

In another aspect of the invention, a method of attaching material adjacent to a metapodial phalangeal joint of a human extremity having a metapodial bone and a proximal phalanx includes forming a metapodial bone tunnel in the metapodial bone, connecting a suture to the material to be attached, placing the suture in the metapodial bone tunnel, threading a first end of a double ended fixation implant into the metapodial bone tunnel in interference fashion to secure the suture relative to the bone tunnel, and separating the first end from a shaft of the fixation implant.

BRIEF DESCRIPTION OF THE DRAWINGS

Various examples of the present invention will be discussed with reference to the appended drawings. These drawings depict only illustrative examples of the invention and are not to be considered limiting of its scope.

FIG. 2 is a dorsal view of the metatarsus and proximal phalanx of the right second metatarsophalangeal joint of the human foot;

FIG. 3 is a medial view of the bones of FIG. 2;

FIG. 4 is a lateral view of the bones of FIG. 2;

FIG. 5A is a perspective view of an illustrative example of a fixation implant according to the present invention;

FIG. 5B is a side detail view of the fixation implant of FIG. 5A;

DESCRIPTION OF THE ILLUSTRATIVE EXAMPLES

The following illustrative examples illustrate fixation implants and methods for making and using them. Implants and methods according to the present invention may be used in conjunction with any surgical fixation procedure but the illustrative examples are shown in a size and form most suitable for fixing native soft tissue and grafts used to reconstruct the soft tissues of joints of the hand and foot. In particular, the illustrative examples depict their use on metatarsophalangeal (MTP) joints of the human foot. The illustrative implants and methods are also suitable for use on metacarpophalangeal (MCP) joints of the human hand. The hand and foot have a similar structure. Each has a volar aspect. In the hand the volar, or palmar, aspect includes the palm of the hand and is the gripping side of the hand. In the foot the volar, or plantar, aspect is the sole of the foot and is the ground contacting surface during normal walking. Both the hand and foot have a dorsal aspect opposite the volar aspect. Both the hand and foot include long bones referred to as metapodial bones. In the hand, the metapodial bones may also be referred to as metacarpal bones. In the foot, the metapodial bones may also be referred to as metatarsal bones. Both the hand and foot include a plurality of phalanges that are the bones of the digits, i.e. the fingers and toes. In both the hand and foot, each of the most proximal phalanges forms a joint with a corresponding metapodial bone. This joint includes a volar plate or band of connective tissue on the volar side of the joint. The joint also includes collateral ligaments on the medial and lateral sides of the joint. A transverse ligament connects the heads of the metapodial bones. In the hand the joint is typically referred to as the metacarpophalangeal joint having a palmar plate on the palmar side, collateral ligaments medially and laterally, and a transverse ligament connecting the metacarpals. In the foot the joint is typically referred to as the metatarsophalangeal joint having a plantar plate on the plantar side, collateral ligaments medially and laterally including proper collateral ligaments and accessory collateral ligaments, and a transverse ligament also known as the transverse metatarsal ligament.

For convenience, the illustrative examples depict the use of devices and techniques according to the present invention to fix soft tissue and grafts used to reconstruct the metatarsophalangeal (MTP) joints of the human foot. The devices and techniques may be used to fix soft tissue or grafts directly and/or they may be used to fix an intermediate material connected to the soft tissue or graft, e.g. a suture strand, leader, sheath, or other intermediate material. The illustrative devices and techniques are also suitable for use on metacarpophalangeal (MCP) joints of the human hand and at other surgical sites. To better orient the reader, the MTP joint and basic anatomic references are explained in more detail below.

Figure 1:
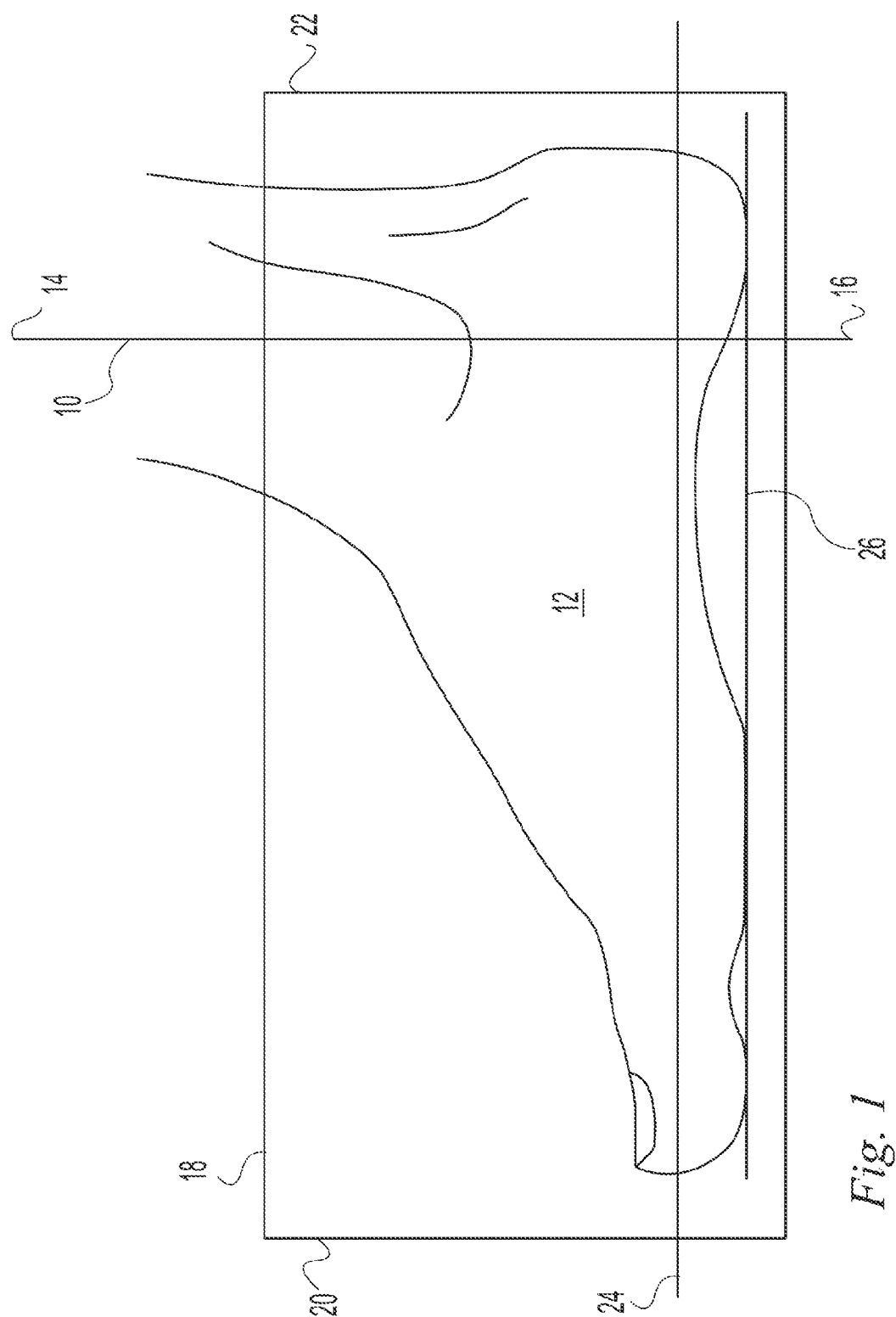
FIG. 1 is a side elevation view of the human foot illustrating anatomic reference planes.

FIG. 1 illustrates the anatomic planes of the foot that are used for reference in this application. The coronal plane 10 extends from the medial aspect 12 to the lateral aspect of the foot and from dorsal 14 to plantar 16 and divides the foot between the toes and heel. The sagittal plane 18 extends anterior 20 to posterior 22 and dorsal 14 to plantar 16 and divides the foot into medial and lateral halves. The transverse plane 24 extends anterior 20 to posterior 22 and medial to lateral parallel to the floor 26.

FIGS. 2-4 illustrate the metatarsus 30 and proximal phalanx 50 of the second MTP joint of the right foot. The medial and lateral epicondyles 32, 34, located on the medial-dorsal and lateral-dorsal aspects of the metatarsus 30 respectively, are the origins of the medial and lateral proper collateral ligaments (PCLs) 36, 38 and the medial and lateral accessory collateral ligaments (ACLs) 40, 42 of the MTP joint. The medial PCL inserts at the medial-plantar aspect 52 and the lateral PCL inserts at the lateral-plantar aspect 54 of the proximal phalanx 50. The ACLs fan out and insert into the plantar plate 44. The metatarsus includes a metatarsal head 46 having an articular surface 48 and the proximal phalanx includes a phalangeal head 56 having an articular surface 58. The metatarsus 30 further includes a longitudinal axis 60 extending lengthwise down the center of the bone.

Figure 5C:
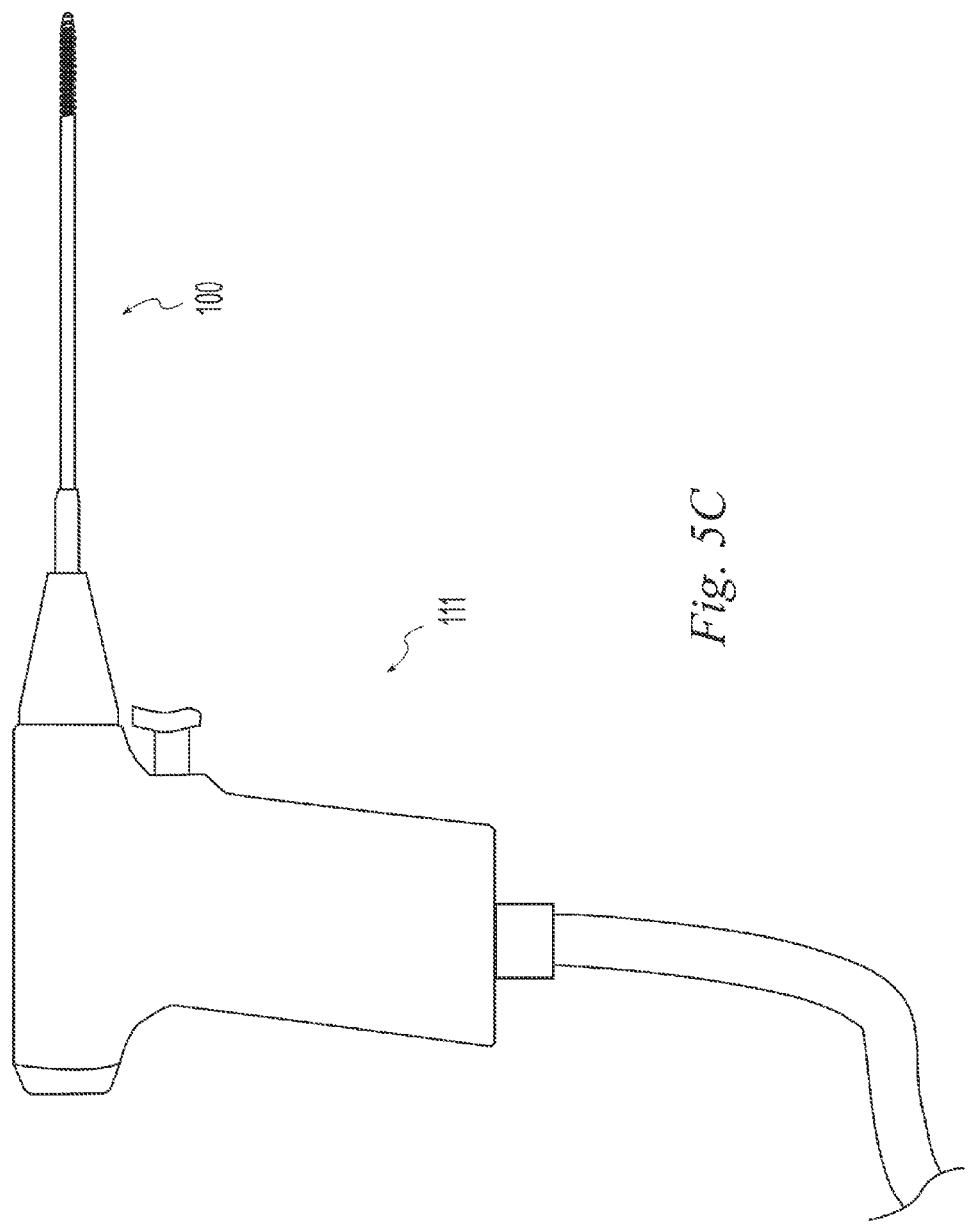
FIG. 5C is a side elevation view of the fixation implant of FIG. 5A loaded into a driver.
Figure 6:
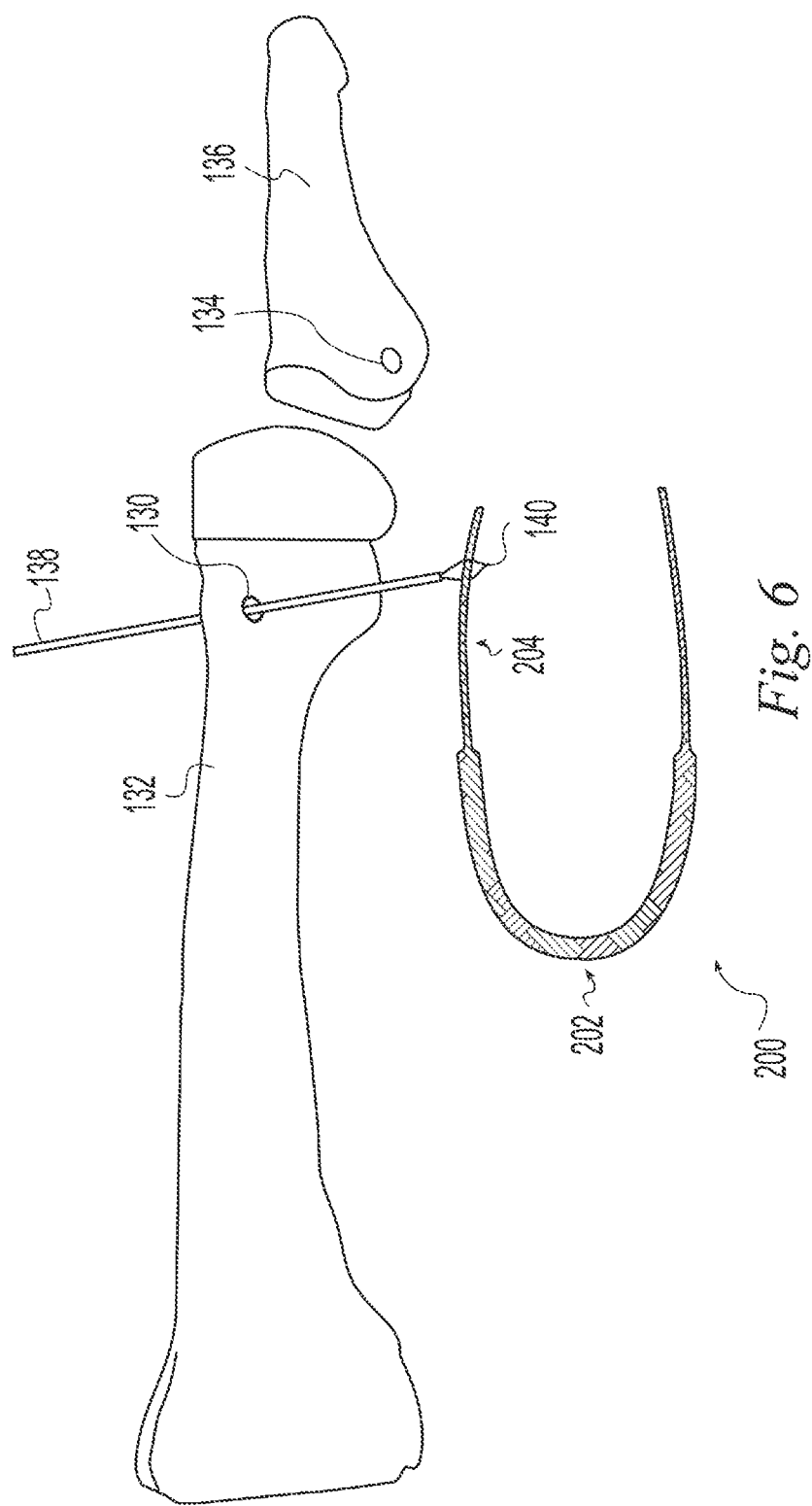
FIGS. 6-12 are side elevation views illustrating steps in a soft tissue reconstruction procedure utilizing the fixation implant of FIG. 5A.

FIGS. 5A-5C illustrate an exemplary fixation implant 100 according to the present invention. The implant 100 includes an elongated shaft 102 having a longitudinal axis 104 and extending from a first end portion 106 to a second end portion 108. An intermediate portion 110 is positioned between the first and second end portion 106, 108. In the illustrative example of FIGS. 5A-C, the intermediate portion 110 is a smooth cylinder suitable for engaging with the chuck of a wire driver 111 and the first and second end portions 106, 108 are threaded to engage a tunnel in a bone. The end portions 106, 108 are separable from the implant, such as by cutting, to permit first one end and then the other to be implanted into a bone tunnel. The implant may be constructed of any biocompatible material that will permit the end portions to be cut to separate them from the rest of the implant. Such materials include metals, polymers, bone, and other suitable materials. Preferably the implant is made of a polymer. More preferably the implant is made of a high performance thermoplastic such as members of the aromatic ketone family of polymers including such polymers as polyetherketone (PEK), polyetheretherketone (PEEK), polyetherketoneketone (PEKK), and other aromatic ketones.

The first end portion 106 has a length 112, the intermediate portion 110 has a length 114, and the second end portion 108 has a length 116 all measured parallel to the longitudinal axis 104. In the illustrative example of FIGS. 5A-5C, the length of the end portions 106, 108 are sized for the longest bone tunnel in which they are expected to be used to provide full threaded engagement over the length of the bone tunnel. The end portions may be the same length, as shown, or they may have different lengths, e.g. if a surgical procedure requires bone tunnels of substantially different length. By sizing for the longest tunnel expected, and not longer, length is preserved for the smooth intermediate portion without making the overall pin length unnecessarily long. In this way the implant is optimized for threaded engagement of the end portions 106, 108 and driver engagement of the intermediate portion. In the illustrative example of FIGS. 5A-5C, the ratio of the length of the intermediate portion to the length of the end portions is in the range of approximately 1:1 to 16:1, preferably in the range of 3:1 to 6:1, and more preferably in the range of 4:1 to 5:1.

For example, in the illustrative implant of FIGS. 5A-5C useful for fixing soft tissue and reconstructive grafts in or adjacent bone tunnels during hand and foot surgery, the end portions are each in the range of approximately 5-18 mm, preferably in the range of 8-15 mm, and more preferably in the range of 10-13 mm while the intermediate portion is in the range of approximately 20-80 mm, preferably in the range of 40-60 mm, and more preferably in the range of 45-55 mm.

In the illustrative example of FIGS. 5A-5C, the end portions 106, 108 are generally cylindrical in outline over most of their length with a conical taper over the terminal portion of the end portion. The taper comes to a blunt point 118 so that the taper is generally frustoconical in shape. The taper length 119 is approximately 5 to 30 percent of the length of each end portion, preferably 10-30 percent of the length, more preferably 15-30 percent of the length.

In the illustrative example of FIGS. 5A-5C, the threads of the end portions 106, 108 are generally flat topped having a major diameter 120, a minor diameter, a pitch 122, a crest width 124, and an intercrest spacing 126. It has been found that secure fixation may be achieved with major diameter 120 to pitch 122 ratios in the range of 0.5:1 to 4:1, preferably 1:1 to 3:1, more preferably 1.5:1 to 2.5:1. In the illustrative example of FIGS. 5A-5C, the major diameter to pitch ratio is approximately 2:1. The crest width 124 influences whether the threads cut into the bone tunnel walls and the repair material, press into them, or merely slide over them. It has been found that good fixation without damage to the soft tissue, graft, or attached sutures occurs when the thread intercrest spacing 126 to crest width 124 ratio is in the range of 1:1 to 3:1, preferably 1.5:1 to 2.5:1. In the illustrative example of FIGS. 5A-5C the intercrest spacing to crest width ratio is approximately 2:1. For example, in the illustrative example of FIGS. 5A-5C, the threads have a major diameter of approximately 1.6 mm, a crest width of approximately 0.26 mm, an intercrest spacing of approximately 0.51 mm, a pitch of approximately 0.76 mm, a threaded portion length 112 of approximately 11.4 mm, and a taper length of approximately 2.16 mm.

FIGS. 6-12 depict an illustrative surgical method utilizing the fixation implant of FIGS. 5A-5C. In the illustrative example of FIGS. 6-12, the implant is shown in use to fix a graft, e.g. a fibrous synthetic graft, used to reconstruct a collateral ligament of a metapodial/phalangeal joint of an extremity of a human patient. In this example, the ligament is the lateral PCL of an MTP joint of a human foot. A tunnel 130 has been formed in the metatarsal bone 132 approximately at the anatomic origin of the lateral PCL. A tunnel 134 has been formed in the proximal phalanx 136 approximately at the insertion of the lateral PCL. A graft passer 138 having a loop 140 is passed through the metatarsal tunnel 130 and an end portion 204 of a graft 200 is inserted through the loop 140.

Figure 7:
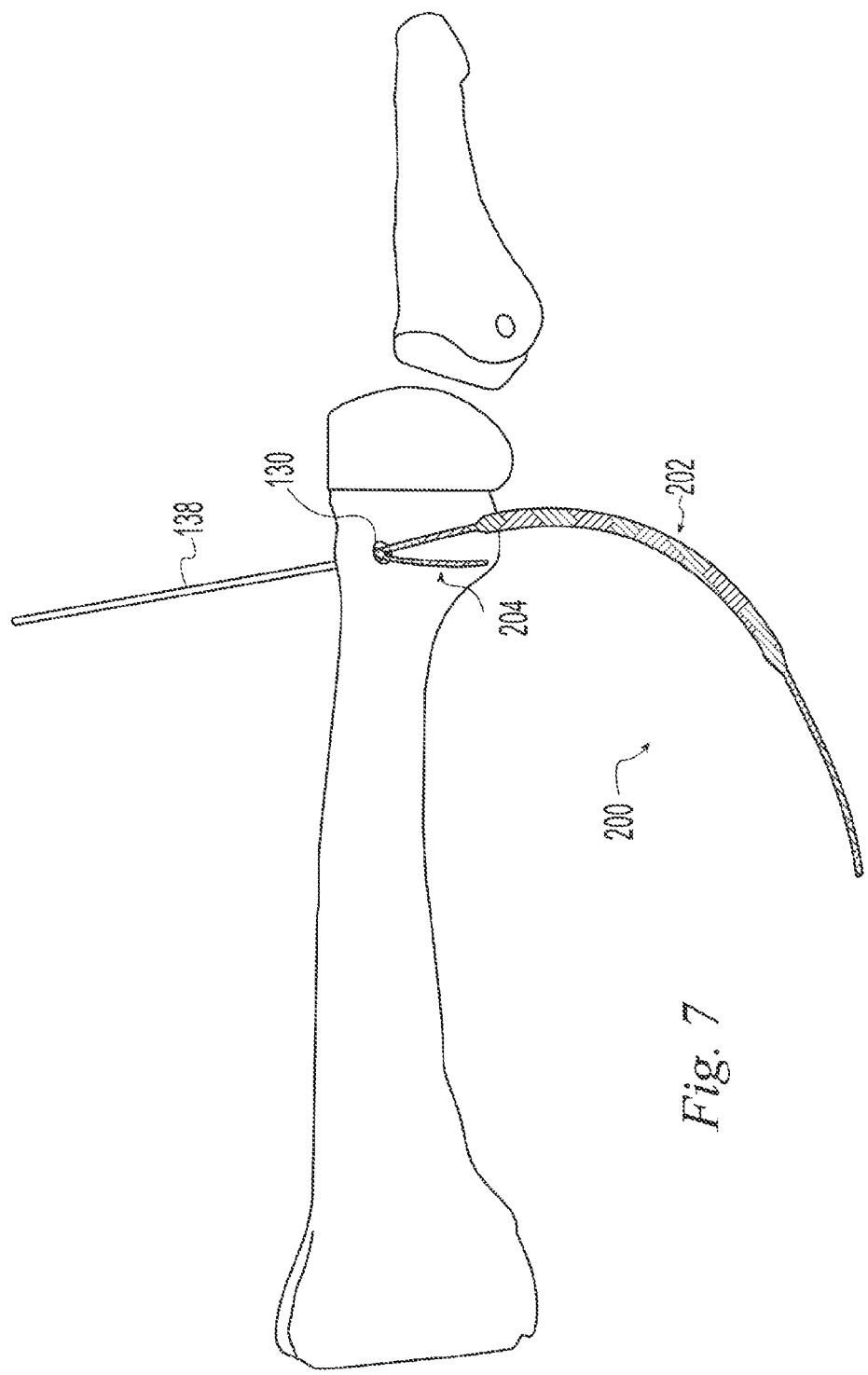

Referring to FIG. 7, the graft passer 138 has been withdrawn pulling the end portion 204 into the tunnel 130. The tunnel 130 is sized for a press fit with an intermediate portion 202 of the graft 200. Because the end portion 204 has a reduced cross sectional area, it is able to fold around the loop 140 and be pulled through the tunnel 130 in a doubled over configuration which allows it to be pulled through the tunnel 130 and without becoming disengaged from the loop 140.

Figure 8:
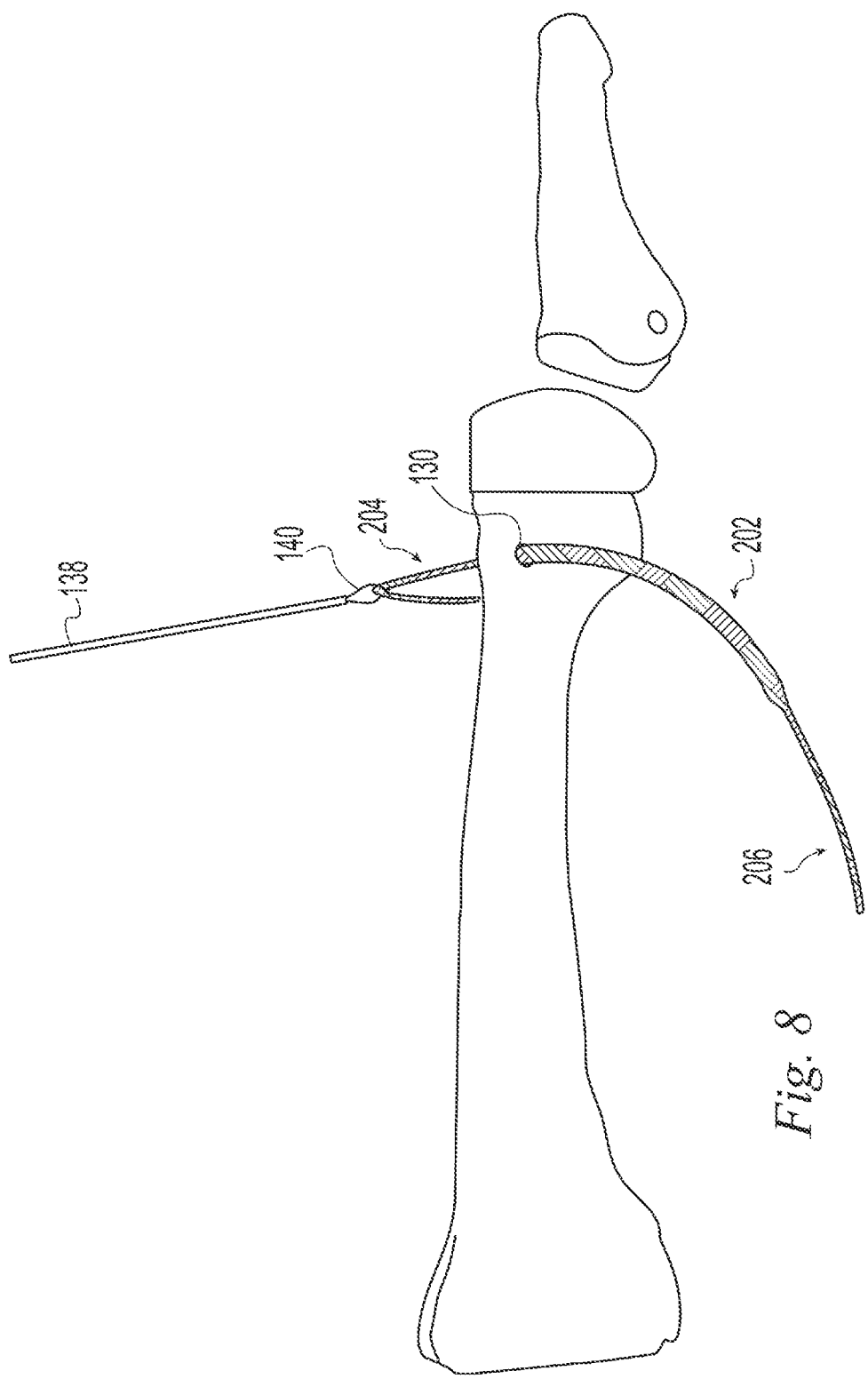

Referring to FIG. 8, the end portion 204 has been pulled through the bone and may be advanced further with the graft passer or by gripping the end portion directly or with another instrument to position the end of the intermediate portion in the bone tunnel.

Figure 9:
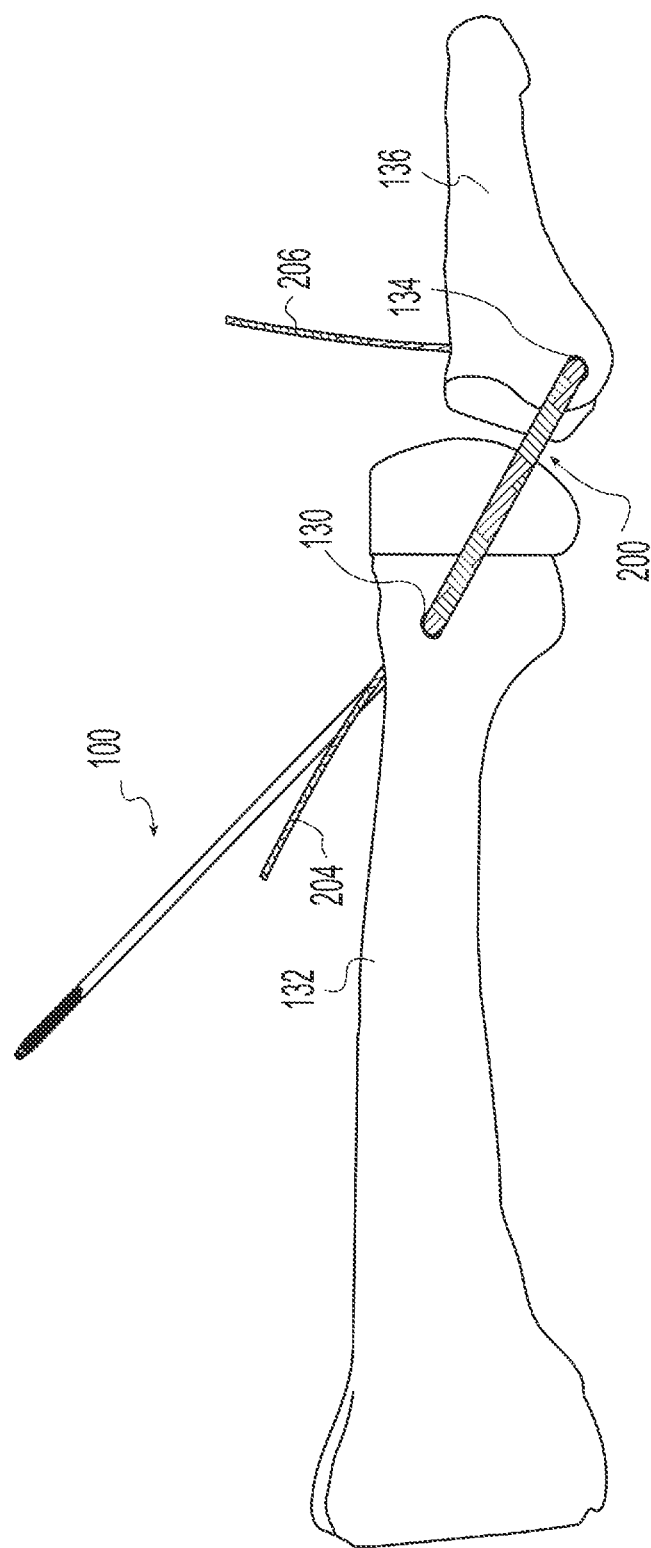

Referring to FIG. 9, one end of the implant 100 has been threaded into the bone tunnel 130 to secure the graft 200 in the bone tunnel in interference fashion with the threads of the implant 100 pressing into the bone tunnel wall and the graft 200. The other of the graft 204 has been passed through the tunnel 134 in the proximal phalanx 136.

Figure 10:
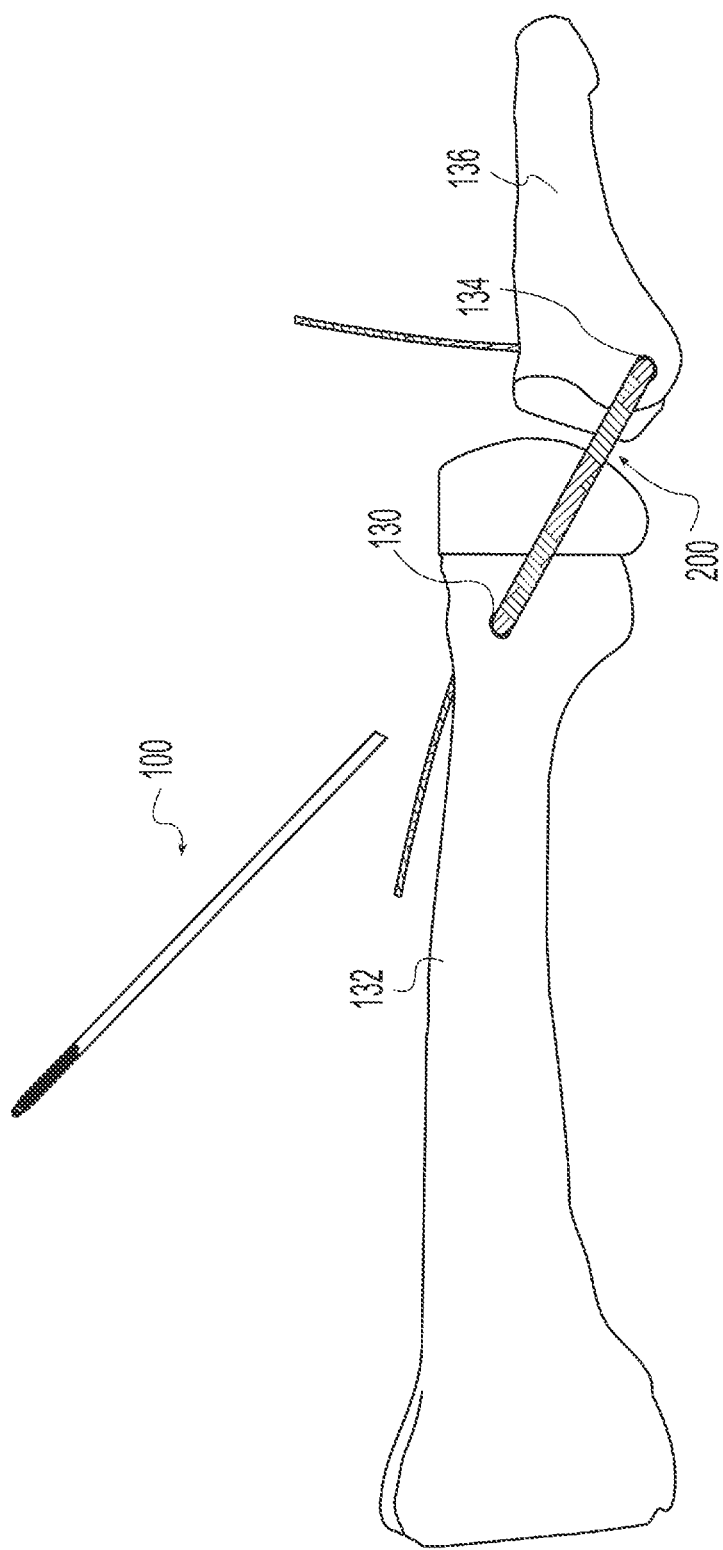

Referring to FIG. 10, the implant has been cut flush with the bone surface in preparation for using the other threaded end to fix the graft 200 in the proximal phalanx 136.

Figure 11:
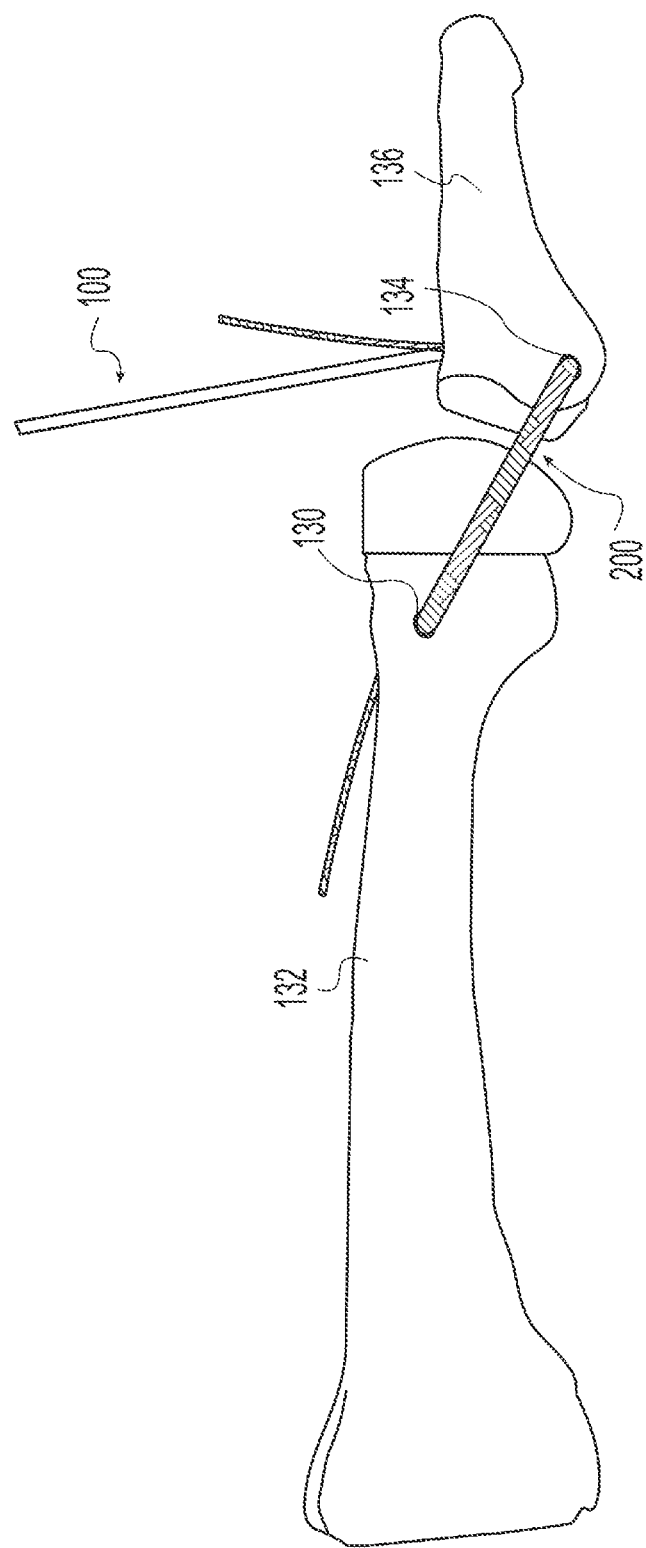

Referring to FIG. 11, the remaining end of the implant 100 has been threaded into the bone tunnel 134 to secure the graft 200 in the bone tunnel in interference fashion with the threads of the implant 100 pressing into the bone tunnel wall and the graft 200.

Figure 12:
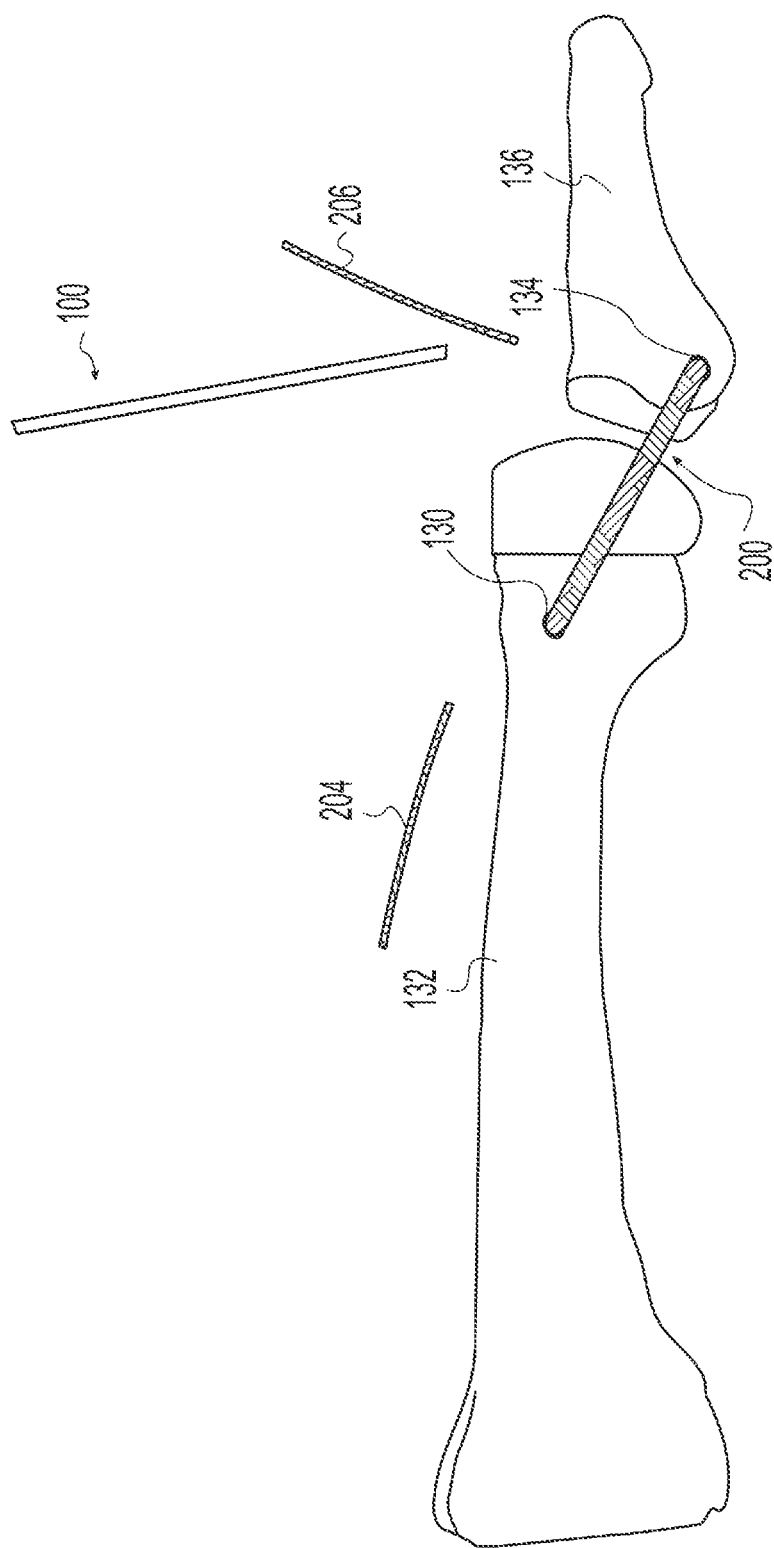

Referring to FIG. 12, the implant has been cut flush with the bone and excess portions of both ends of the graft 200 have been cut and removed from the surgical site.

Figure 13:
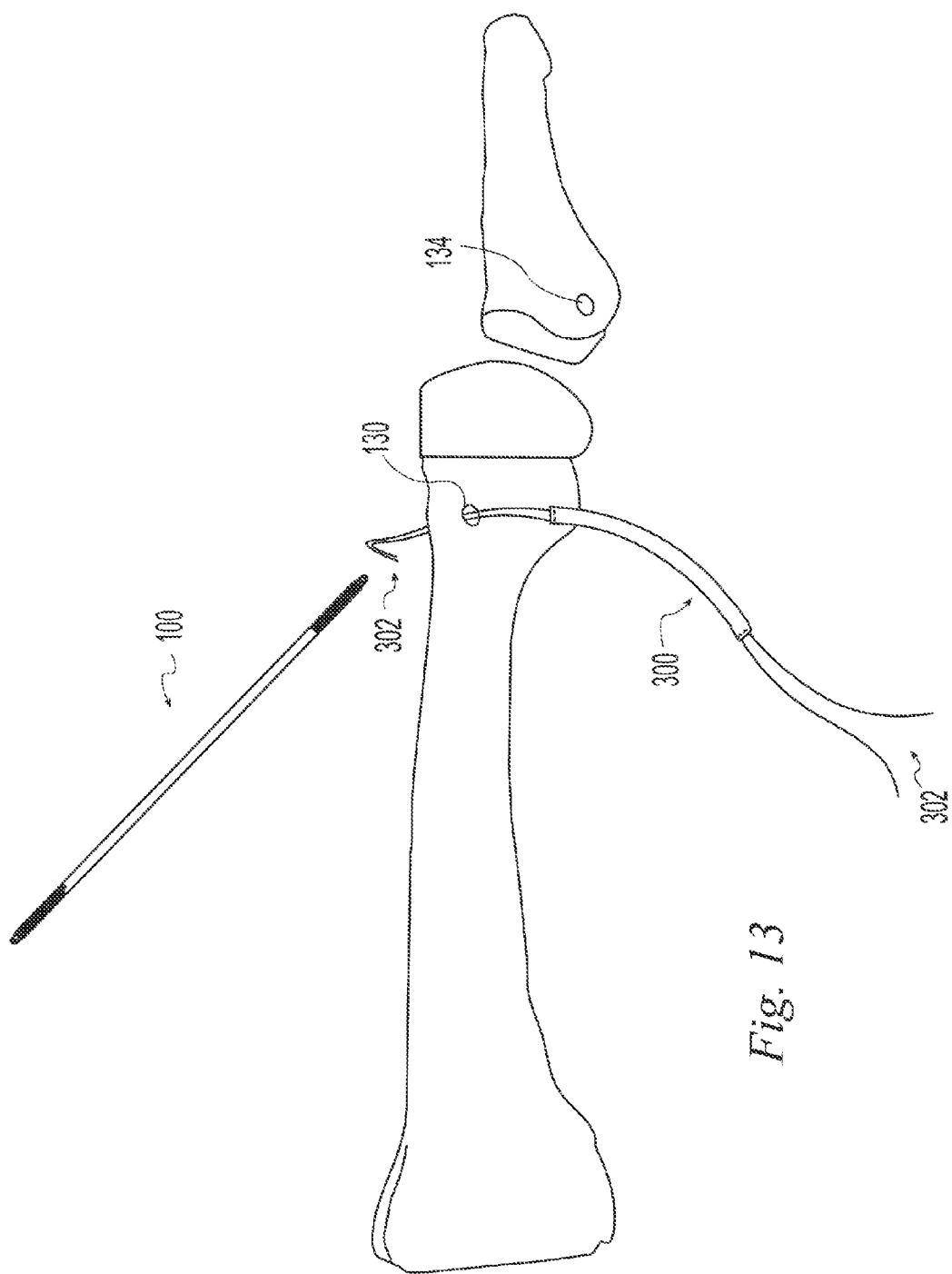
FIG. 13 is a side elevation view illustrating a soft tissue reconstruction procedure utilizing the fixation implant of FIG. 5A.

Referring to FIG. 13, a graft 300, e.g. a tissue graft, has sutures 302 attached, e.g. by stitching, to its ends. As described above, a graft passer 138 having a loop is used to pass the sutures 302 into the bone tunnels 130, 134. However, in the illustrative example of FIG. 13, the sutures 302 and not the graft are fixed in the bone tunnel by the fixation implant 100 and the sutures 302 support the graft. Similarly, the fixation implant 100 may be used to fix sutures that are attached to torn, stretched, or detached native soft tissues in order to reattach and/or repair the native soft tissues.

Figure 14:
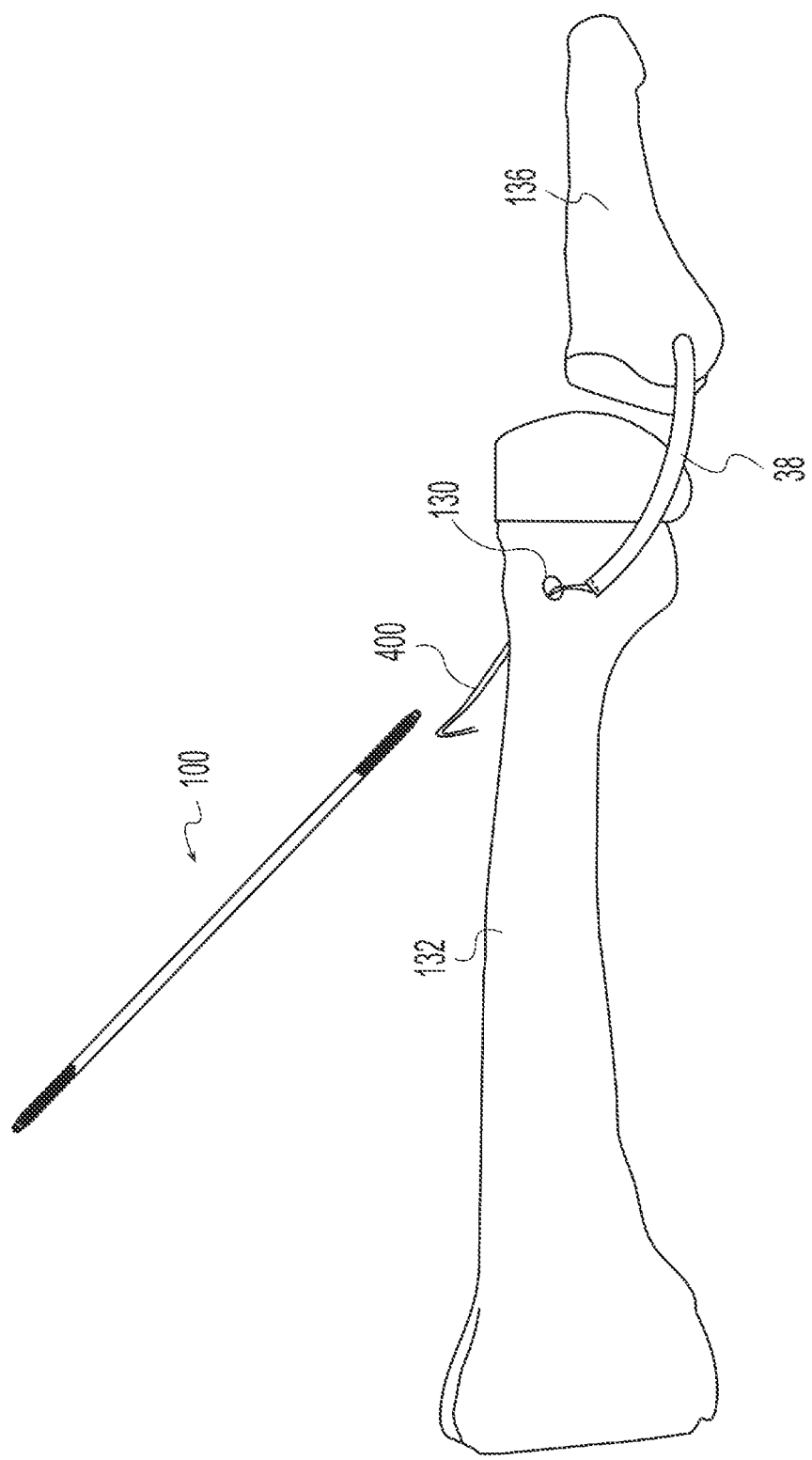
FIG. 14 is a side elevation view illustrating a soft tissue reconstruction procedure utilizing the fixation implant of FIG. 5A.

Referring to FIG. 14, a collateral ligament has been released or avulsed from its origin on the metatarsal bone 132. For example, the ligament may be released to provide enhanced access to another part of the joint to facilitate a surgical repair such as for example to gain access to the plantar plate. Alternatively, an injury or chronic condition may have led to the ligament becoming detached from its anatomic origin. In the illustrative example of FIG. 14, the lateral PCL 38 has been detached to provide access for a primary surgical procedure. After the primary surgical procedure has been accomplished, the lateral PCL 38 is reattached by forming a bone tunnel 130 in the metatarsal bone 132, attaching sutures 400 to the free end of the ligament, passing the sutures into, or through as shown in the illustrative example of FIG. 14, the bone tunnel 130, tensioning the sutures, and fixing the sutures with the fixation implant 100. For example, the fixation implant 100, may be threaded into the bone tunnel 130 to form an interference fit between the bone and suture 400 and lock the sutures in place. The portion of the fixation implant 100 protruding from the bone is then cut off and the other end of the fixation implant 100 may be used to fix other material. For example in a bilateral procedure the other end of the fixation implant 100 may be used to fix sutures connected to the medial collateral ligament.

The illustrative examples have depicted a fixation implant constructed and used for graft fixation in reconstruction of an MTP joint of a human foot. The graft and methods of the present invention are suitable for grafting at other locations within a patient's body including, but not limited to, the MCP joints of the human hand.

What is claimed is:

1. A method of attaching material adjacent to a metapodial phalangeal joint of a human extremity utilizing a fixation implant, the fixation implant comprising an elongated, unitary shaft having a longitudinal axis and extending from a first end portion to a second end portion and having an intermediate portion between the first and second end portions, the intermediate portion being substantially smooth and the end portions being threaded, the joint including a metapodial bone and a proximal phalanx, the method comprising:
   forming a bone tunnel in the metapodial bone;
   forming a bone tunnel in the proximal phalanax;
   approximating a first portion of the material near the metapodial bone tunnel;
   threading the first end portion of the fixation implant into the metapodial bone tunnel in interference fashion to secure the first portion of the material relative to the metapodial bone tunnel;
   separating the first end portion from the intermediate portion of the fixation implant by cutting the first end portion;
   approximating a second portion of the material near the proximal phalangeal bone tunnel;
   threading the second end portion of the fixation implant into the proximal phalangeal bone tunnel in interference fashion to secure the second portion of the material relative to the proximal phalangeal bone tunnel; and
   separating the second end portion from the intermediate portion of the fixation implant by cutting the second end portion.

2. The method of claim 1 wherein the metapodial bone is a metatarsal bone and the metapodial phalangeal joint is an MTP joint of a human foot and the metapodial bone tunnel intersects the origin of a proper collateral ligament and the phalangeal bone tunnel intersects the insertion of the proper collateral ligament.

3. The method of claim 1 wherein the metapodial bone is a metatarsal bone and the metapodial phalangeal joint is an MTP joint of a human foot and the metapodial bone tunnel intersects the origin of an accessory collateral ligament and the phalangeal bone tunnel intersects the insertion of the accessory collateral ligament.

4. The method of claim 1 further comprising:
   connecting a suture to the material to be attached;
   placing the suture in the metapodial bone tunnel; and
   securing the suture in the bone tunnel during the step of threading the first end portion of the fixation implant into the metapodial bone tunnel in interference fashion to secure the first portion of the material relative to the metapodial bone tunnel.

5. The method of claim 4 wherein the material comprises a collateral ligament.

6. The method of claim 5 wherein the collateral ligament is one of a medial and lateral collateral ligament.

7. The method of claim 1 wherein the material to be attached is a graft, the method further comprising connecting a first suture to a first end of the graft and connecting a second suture to a second end of the graft.

8. The method of claim 7 wherein the graft is selected from the group consisting of a fibrous synthetic graft and a tissue graft.

9. The method of claim 1 further comprising passing a graft passer through at least one of the bone tunnels.

10. The method of claim 1 further comprising loading the intermediate portion of the fixation implant in a wire driver.

11. The method of claim 1 wherein securing the material includes threading the fixation implant into the bone tunnel such that the fixation implant presses the material against a bone tunnel wall.

12. The method of claim 1 wherein the fixation implant is cut flush with a bone surface.

13. The method of claim 4 wherein the step of approximating a first portion of the material near the metapodial bone tunnel and the step of approximating a second portion of the material near the proximal phalangeal bone tunnel includes passing the suture into the metapodial and proximal phalangeal bone tunnels.

14. The method of claim 4 further comprising tensioning the suture.

15. A method of attaching material adjacent to a metapodial phalangeal joint of a human extremity, the joint including a metapodial bone and a proximal phalanx, the method comprising:

forming a bone tunnel in the metapodial bone;
engaging an intermediate portion of a fixation implant with a chuck of a wire driver such that a first end portion of the fixation implant is available for use;
approximating a first portion of the material near the metapodial bone tunnel;
threading a threaded first end portion of the fixation implant into the metapodial bone tunnel in interference fashion to secure the first portion of the material relative to the metapodial bone tunnel;
separating the first end portion from the intermediate portion of the fixation implant by cutting the first end portion;
removing the intermediate portion from the wire driver chuck;
engaging the intermediate portion of the fixation implant with the wire driver chuck such that a second end portion of the fixation implant is available for use;
forming a bone tunnel in the proximal phalanx;
approximating a second portion of the material near the proximal phalangeal bone tunnel;
threading a threaded second end portion of the fixation implant into the proximal phalangeal bone tunnel in interference fashion to secure the second portion of the material relative to the proximal phalangeal bone tunnel; and
separating the second end portion from the intermediate portion of the fixation implant by cutting the second end portion.

16. The method of claim 15 further comprising attaching sutures to the material.

17. The method of claim 15, wherein the material is selected from the group consisting of a joint tissue and a graft.

* * * * *